United States Patent [19]

Fuchs et al.

[11] Patent Number: 4,837,362
[45] Date of Patent: Jun. 6, 1989

[54] PREPARATION OF PURE HYDROXYLAMMONIUM SALTS OF FATTY ACIDS OF 1 TO 4 CARBON ATOMS

[75] Inventors: Hugo Fuchs, Ludwigshafen; Franz-Josef Weiss, Neuhofen, both of Fed. Rep. of Germany

[73] Assignee: BASF Aktiengesellschaft, Ludwigshafen, Fed. Rep. of Germany

[21] Appl. No.: 3,658

[22] Filed: Jan. 15, 1987

[30] Foreign Application Priority Data

Jan. 17, 1986 [DE] Fed. Rep. of Germany ....... 3601216

[51] Int. Cl.$^4$ .............................................. C07C 51/41
[52] U.S. Cl. .................................... 562/606; 562/607; 562/608; 562/609
[58] Field of Search ................ 562/606, 607, 608, 609

[56] References Cited

U.S. PATENT DOCUMENTS

| | | | |
|---|---|---|---|
| 2,483,252 | 9/1949 | Tryon | 562/606 X |
| 3,336,375 | 8/1967 | Jones | 562/607 X |
| 3,966,804 | 6/1976 | Bathellier et al. | 562/609 |
| 4,507,248 | 3/1985 | Mathew et al. | 260/500.5 |

FOREIGN PATENT DOCUMENTS

108294 5/1984 European Pat. Off. .

OTHER PUBLICATIONS

Gmelins Handbook of Inorganic Chemistry, 8th ed., p. 599, Line 27–28, Verlay Chemie, Weinheim Publishers.

*Primary Examiner*—Werren B. Lone
*Attorney, Agent, or Firm*—Keil & Weinkauf

[57] ABSTRACT

Pure hydroxylammonium salts of fatty acids of 1 to 4 carbon atoms are prepared by reacting hydroxylammonium sulfate and alkali metal salts of fatty acids with 1 to 4 carbon atoms in solution at elevated temperatures and separating off the hydroxylammonium salts of fatty acids of 1 to 4 carbon atoms by (a) reacting hydroxylammonium sulfate and alkali metal salts of fatty acids of 1 to 4 carbon atoms in solution in water or alkanols of 1 to 3 carbon atoms or mixtures thereof at 20°–70° C.,
(b) evaporating the solvent out of the reaction mixture to obtain a dry residue,
(c) isolating the hydroxlammonium salts of fatty acids of 1 to 4 carbon atoms from the dry residue thus obtained by sublimation under reduced pressure.

3 Claims, No Drawings

PREPARATION OF PURE HYDROXYLAMMONIUM SALTS OF FATTY ACIDS OF 1 TO 4 CARBON ATOMS

U.S. Pat. No. 2,483,252 discloses a process for preparing hydroxylammonium salts of lower fatty acids by reacting hydroxylammonium chloride or sulfate with alkali metal salts of lower fatty acids in alcoholic solution at elevated temperatures. After cooling, alkali metal sulfate or chloride is crystallized out and separated off, and subsequently the alcoholic solution of hydroxylammonium salts of lower fatty acids is evaporated and the salts are isolated by crystallization. This process has the disadvantage that the resulting hydroxylammonium salts of lower fatty acids are not free of foreign ions, since crystallization is not a very effective method for preventing contamination. On the other hand, further purification by fractional crystallization is very costly.

It is an object of the present invention to provide a process for preparing pure hydroxylammonium salts of lower fatty acids which in a simple manner prevents the contamination of the product by foreign ions.

We have found that this object is achieved with a process for preparing a pure hydroxylammonium salt of a fatty acid of 1 to 4 carbon atoms by reacting hydroxylammonium sulfate and an alkali metal salt of a fatty acid in solution at elevated temperatures and separating off the hydroxylammonium salt of the fatty acid of 1 to 4 carbon atoms, which comprises (a) reacting hydroxylammonium sulfate and an alkali metal salt of a fatty acid of 1 to 4 carbon atoms in aqueous solution or dissolved in an alkanol of 1 to 3 carbon atoms or a mixture thereof at 20°–70° C., (b) evaporating the solvent out of the reaction mixture to obtain a solvent-free residue, (c) isolating from the dry residue thus obtained the hydroxylammonium salt of the fatty acid of 1 to 4 carbon atoms by sublimation under reduced pressure.

The novel process has the advantage that hydroxylammonium salts of fatty acids of 1 to 4 carbon atoms are obtained in high purity. The novel process further has the advantage that it is inexpensive.

According to the invention, the starting material is hydroxylammonium sulfate. Advantageously the hydroxylammonium sulfate used has an ammonium ion content of less than 500 ppm, in particular less than 100 ppm. Hydroxylammonium sulfate of this type is advantageously obtained by multiple, for example double or triple, crystallization from aqueous solution. This is advantageously done by evaporating the aqueous solution of hydroxylammonium sulfate at 48°–80° C. and 50–400 mbar, cooling and isolating crystallized hydroxylammonium sulfate. By repeated crystallization it is possible to bring the ammonium ion content of the hydroxylammonium sulfate to the aforementioned value.

The second reactant used is an alkali metal salt of a fatty acid of 1 to 4 carbon atoms. Preferred alkali metal salts are the salts of sodium or potassium, in particular the sodium salts of the acids mentioned. Suitable starting materials are, for example, sodium formate, sodium acetate, potassium acetate, sodium propionate or potassium butyrate. The salts can be present in anhydrous form or contain crystal water. It is preferred to use an alkali metal salt of acetic acid. Consequently hydroxylammonium acetate is a preferred product.

The reaction is carried out in alcoholic or aqueous solution or mixtures thereof. Examples of suitable alkanols of 1 to 3 carbon atoms are methanol, ethanol and propanol. Methanol is particularly preferred.

The starting materials are expediently mixed in the form of alcoholic or aqueous solutions. Expediently the solutions used contain from 10 to 50% by weight of a hydroxylammonium sulfate on the one hand and an alkali metal salt of one of the fatty acids mentioned on the other. It is also possible to introduce first one of the reactants, for example hydroxylammonium sulfate, in the form of a solution and to add an alkali metal salt of one of the fatty acids mentioned in finely divided solid form, or vice versa. A further version of the process comprises introducing a solution of hydroxylammonium sulfate first and producing an alkali metal salt of one of the fatty acids mentioned in situ by adding the desired fatty acid, for example acetic acid, and neutralizing it with an equivalent amount of sodium hydroxide solution.

The hydroxylammonium sulfate and the alkali metal salt of one of the fatty acids mentioned are advantageously employed in a molar ratio of 1:1. It has proved useful to carry out the reaction at 20°–70° C., in particular 40°–60° C.

According to the invention, the solvent of the reaction mixture thus obtained, which in addition to the solvent used now contains the hydroxylammonium salt of one of the fatty acids mentioned and an alkali metal sulfate, is evaporated until a dry residue is obtained. Advantageously a temperature of 5° to 60° C. is employed for the evaporating step. If the boiling point of the solvent used is higher, the evaporating of the solvent is carried out under reduced pressure, for example 5–500 mbar.

From the dry residue thus obtained, which comprises a solid hydroxylammonium salt of one of the fatty acids mentioned and an alkali metal sulfate, the hydroxylammonium salt obtained in each particular case is isolated by sublimation under reduced pressure. Advantageously the sublimation is carried out at 10°–50° C. and 0.1–200 mbar.

By means of the process according to the invention it is possible to prepare hydroxylammonium salts of fatty acids in a purity of greater than 99%. The hydroxylammonium acetate obtainable by the invention is suitable, for example, for reacting carbonyl compounds in organic solvents.

The process of the invention is illustrated by the following examples.

EXAMPLE 1

Preparation of Hydroxylammonium Acetate 82 g (0.5 mol) of hydroxylammonium sulfate with an ammonium ion content of 100 ppm are mixed with 100 g of water. 136 g of sodium acetate trihydrate in 100 g of water are added at 40° C. The pH of the solution is 5.6. The solution is subsequently evaporated to dryness at about 50° C. under reduced pressure in a rotary evaporator. The residue amounts to 160 g. The reaction mixture is then transferred to a sublimation apparatus and sublimed at 40° C. and 0.5 mbar. The sublimate obtained is 91 g of hydroxylammonium acetate having a purity of 99.5%. The nonsublimable residue comprises sodium sulfate with traces of hydroxylammonium acetate.

EXAMPLE 2

Preparation of Hydroxylammonium Propionate 74 g of propionic acid are converted with 40 g of sodium hydroxide in 180 ml of water into the sodium salt of propionic acid. 82 g of hydroxylammonium sulfate having an ammonium ion content of less than 500 ppm in 100 ml of water are then added at 40° C. The solution is stripped of water as described in Example 1, leaving a residue of 174 g, which is sublimed at 40° C. and 0.5 mbar. The sublimate obtained is 101 g of hydroxylammonium propionate having a purity of 99.2%.

We claim:

1. A process for preparing a pure hydroxylammonium salt of a fatty acid of 1 to 4 carbon atoms by
    (a) reacting hydroxylammonium sulfate and an alkali metal salt of a fatty acid of 1 to 4 carbon atoms in solution in water or an alkanol of 1 to 3 carbon atoms or a mixture thereof at 20°–70° C.,
    (b) evaporating the solvent out of the reaction mixture at 5°–60° C. and 5–500 mbar to obtain a dry residue,
    (c) isolating from the dry residue thus obtained the hydroxylammonium salt of the fatty acid of 1 to 4 carbon atoms by sublimination at 10°–50° C. and under a reduced pressure of 0.1–200 mbar.

2. The process as claimed in claim 1, wherein the solvent used is water, methanol or a mixture thereof.

3. The process as claimed in claim 1, wherein the starting materials used are hydroxylammonium sulfate and sodium acetate trihydrate.

* * * * *